(12) United States Patent
Matsuhana et al.

(10) Patent No.: US 11,450,502 B2
(45) Date of Patent: Sep. 20, 2022

(54) X-RAY IMAGING APPARATUS AND CONSUMPTION LEVEL ESTIMATION METHOD FOR X-RAY SOURCE

(71) Applicant: Shimadzu Corporation, Kyoto (JP)

(72) Inventors: Bunta Matsuhana, Kyoto (JP); Goro Kambe, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 30 days.

(21) Appl. No.: 17/139,122

(22) Filed: Dec. 31, 2020

(65) Prior Publication Data

US 2022/0208502 A1    Jun. 30, 2022

(51) Int. Cl.
*H01J 35/14* (2006.01)
*H01J 35/04* (2006.01)
(Continued)

(52) U.S. Cl.
CPC ............ *H01J 35/045* (2013.01); *A61B 6/54* (2013.01); *H01J 35/06* (2013.01); *H05G 1/52* (2013.01); *H01J 2235/08* (2013.01)

(58) Field of Classification Search
CPC ............ H05G 1/26; H05G 1/54; H05G 1/025; H05G 1/06; H05G 1/265; H05G 1/56; H05G 1/10; H05G 1/60; H05G 1/62; H05G 1/30; H05G 1/34; H05G 1/08; H05G 1/085; H05G 1/02; H05G 1/52; H05G 1/32; G01N 23/04; G01N 23/043; G01N 2223/304; G01N 2223/3307; G01N 2223/5015;
(Continued)

(56) References Cited

U.S. PATENT DOCUMENTS

| 5,398,274 A | 3/1995 | Komatani et al. |
| 2004/0136499 A1* | 7/2004 | Holland .................. H01J 35/10 378/119 |

(Continued)

FOREIGN PATENT DOCUMENTS

| JP | H05188018 A | 7/1993 |
| WO | 2003/092336 A1 | 11/2003 |

OTHER PUBLICATIONS

Japanese Office Action dated Aug. 31, 2021, in connection with corresponding JP Application No. 2018-175609 (8 pp., including machine-generated English translation).

*Primary Examiner* — Irakli Kiknadze
(74) *Attorney, Agent, or Firm* — Maier & Maier, PLLC

(57) ABSTRACT

An X-ray imaging apparatus and a consumption level estimation method for an X-ray source, which estimate the consumption level of an X-ray source without measuring grid voltage. An X-ray control part includes: a tube current value setting part setting a tube current value supplied to an X-ray source; a tube current value measurement part measuring a cathode current value as the tube current value by a cathode current detector; a time measurement part measuring the time when the tube current value is set by the tube current value setting part and the time when the tube current value measured by the tube current value measurement part reaches the set value; and a consumption level estimation part estimating the consumption level of a cathode in the X-ray source based one the time until the tube current value reaches the set value after the tube current value has been set.

4 Claims, 5 Drawing Sheets

(51) Int. Cl.
*A61B 6/00* (2006.01)
*H05G 1/52* (2006.01)
*H01J 35/06* (2006.01)

(58) Field of Classification Search
CPC .. G01N 2223/406; G01N 23/22; G01N 23/20; G01N 23/223; G01N 2223/076; G01N 23/083; G01N 2223/204; G01N 2223/04; G01N 23/046; G01N 2201/022; G21K 5/02; H01J 35/18; H01J 35/04; H01J 35/025; H01J 37/3405; H01J 37/3444; H01J 35/116; H01J 37/242; H01J 37/243; H01J 37/244; H01J 35/045; H01J 35/06; H01J 2235/08; H01J 35/064; H01J 35/066; H01J 35/10; H01J 35/065; H01J 3/021; H05H 1/0081; G01T 1/00; G01T 7/00; A61B 6/54; G21F 7/00; H04N 5/32; G06T 7/001
USPC .......................................................... 378/138
See application file for complete search history.

(56) References Cited

U.S. PATENT DOCUMENTS

| | | | |
|---|---|---|---|
| 2005/0069086 A1* | 3/2005 | Deych | A61B 6/482 378/112 |
| 2006/0008053 A1 | 1/2006 | Ishikawa et al. | |
| 2014/0348291 A1* | 11/2014 | Lee | A61B 6/0414 378/208 |

* cited by examiner

X-RAY IMAGING APPARATUS AND CONSUMPTION LEVEL ESTIMATION METHOD FOR X-RAY SOURCE

FIELD

The present invention relates to an X-ray imaging apparatus including an X-ray source that gives high voltage between a cathode and a target, as well as keeps a tube current value at a set value by performing feedback control of grid voltage given to a grid disposed between the cathode and the target, and to a consumption level estimation method for the X-ray source.

BACKGROUND

When imaging an image using an X-ray imaging apparatus, an X-ray source is given tube voltage and tube current adapted to imaging of an object. In such an X-ray source, feedback control is performed which, in a state where a predetermined tube voltage is applied between a cathode and a target, adjusts grid voltage to be applied to a grid electrode arranged in the vicinity of the cathode between the cathode and the target so that a tube current value becomes constant, and thereby matches the tube current value with a set value.

It is known that in such an X-ray source, the consumption level of the cathode can be determined from the value of the grid voltage at the time of controlling the tube current value to the set value (see Patent Literature 1). That is, it can be determined that even when the potential difference between the grid and the cathode is large, when the tube current is detectable, the consumption level is low, whereas when unless the potential difference between the grid and the cathode is decreased, the tube current is undetectable, the consumption of the cathode progresses.

CITATION LIST

Patent Literatures

Patent Literature 1: International Publication No. WO2003/092336

SUMMARY

In order to measure the consumption level of a cathode by the above-described conventional method, grid voltage has to be measured. However, a grid electrode is arranged in an X-ray tube, and therefore it is difficult to measure the voltage value of the grid voltage from outside the X-ray tube. For this reason, the grid voltage has to be preliminarily designed to be taken out via a control circuit or the like of an X-ray source. Accordingly, an X-ray source incapable of measuring grid voltage from the outside has the problem of being unable to measure the consumption level of a cathode.

The present invention has been made in order to solve the above-described problem, and intends to provide an X-ray imaging apparatus and a consumption level estimation method for an X-ray source, which are capable of estimating the consumption level of an X-ray source without measuring grid voltage.

A first aspect of the present invention includes: an X-ray source that gives high voltage between a cathode and a target, as well as keeps a tube current value at a set value by performing feedback control of grid voltage given to a grid disposed between the cathode and the target; a tube current value setting part that sets the tube current value; and a time measurement part that measures the time when the tube current value is set and the time when the tube current value reaches the set value.

A second aspect of the present invention includes a consumption level estimation part that estimates the consumption level of the X-ray source on the basis of the time until the tube current value reaches the set value after the tube current value has been set.

A third aspect of the present invention includes an alarm display part that displays an alarm when the time until the tube current value reaches the set value after the tube current value has been set exceeds a preset set time.

A fourth aspect of the present invention includes a control unit that, when performing aging on the X-ray source, performs measurement of the time until the tube current value reaches the set value after the tube current value has been set.

A fifth aspect of the present invention is a consumption level estimation method for an X-ray source that gives high voltage between a cathode and a target, as well as keeps a tube current value at a set value by performing feedback control of grid voltage given to a grid disposed between the cathode and the target, and the consumption level estimation method estimates the consumption level of the X-ray source on the basis of the time until the tube current value reaches the set value after the tube current values has been set.

According to the first and fifth aspects of the present invention, the consumption level of the X-ray source can be estimated by using the time when the tube current value is set and the time when the tube current value reaches the set value. For this reason, the consumption level of the X-ray source can be estimated without measuring the grid voltage.

According to the second aspect of the present invention, since the consumption level of the X-ray source is estimated on the basis of the time until the tube current value reaches the set value after the tube current value has been set, the consumption level of the X-ray source can be estimated without measuring grid voltage.

According to the third aspect of the present invention, since the alarm display part that displays the alarm when the time until the tube current value reaches the set value after the tube current value has been set exceeds the preset set time is included, the alarm can be given on the basis of the consumption level of the X-ray source without measuring the grid voltage.

According to the fourth aspect of the present invention, since when performing the aging, the measurement of the time until the tube current value reaches the set value after the tube current value has been set is performed, the time until the tube current value reaches the set value can be measured under the same conditions, thus making it possible to more accurately estimate the consumption level of the X-ray source.

DETAILED DESCRIPTION

Figure 1:
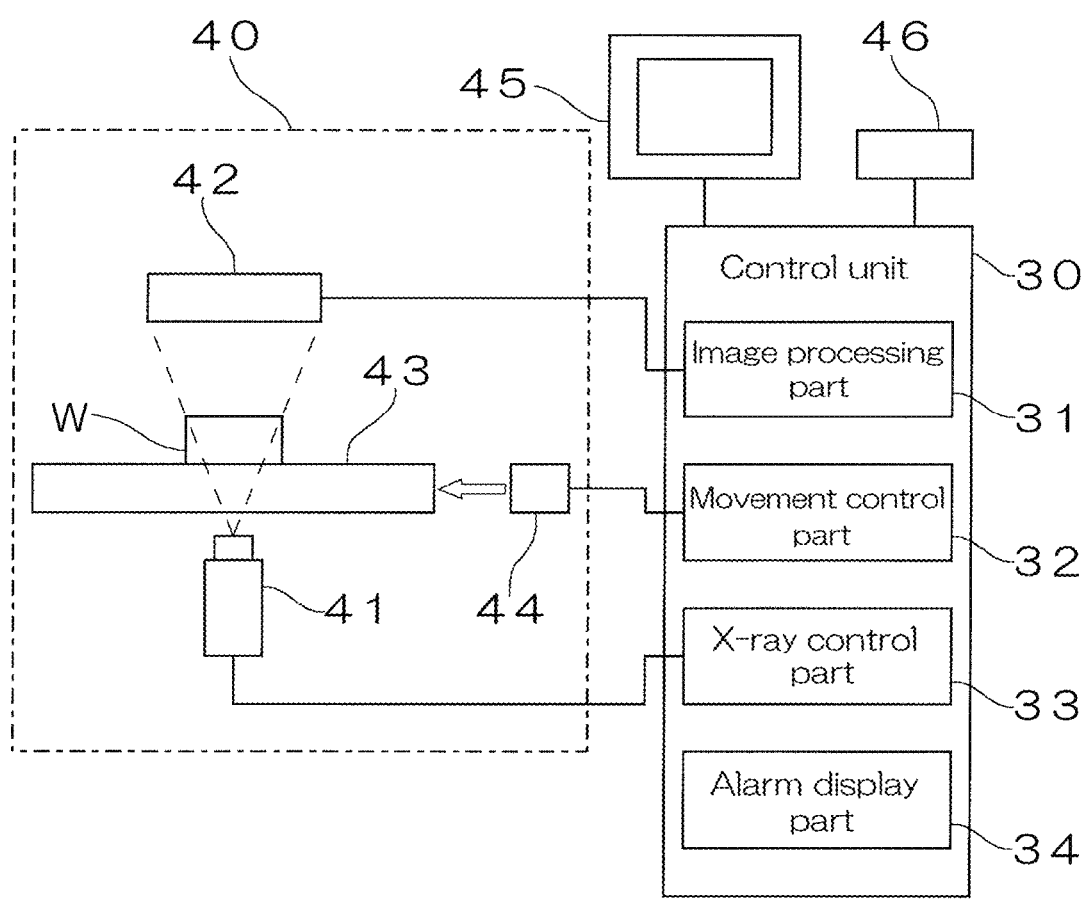
FIG. 1 is a schematic diagram illustrating the X-ray imaging apparatus according to the present invention together with the main control system of the apparatus.

In the following, an embodiment of the present invention will be described on the basis of the drawings. FIG. 1 is a schematic diagram illustrating the X-ray imaging apparatus according to the present invention together with the main control system of the apparatus.

The X-ray imaging apparatus according to the present invention includes: an X-ray source 41 that irradiates a work W as a test object with X-rays; an X-ray detector 42 that detects X-rays transmitting through the work W after the irradiation from the X-ray source 41, such as a flat panel detector or an image intensifier (I. I.); and a stage 43 that is disposed between the X-ray source 41 and the X-ray detector 42 and for placing the work W. The stage 43 is adapted to be horizontally movable in two mutually orthogonal directions by action of a stage moving mechanism 44 provided with an unillustrated motor. The X-ray source 41, the X-ray detector 42, the stage 43, and the stage moving mechanism 44 are disposed inside a casing 40 formed of an X-ray shielding member. The stage moving mechanism 44 may be configured to be vertically movable.

The X-ray imaging apparatus according to the present invention is provided with a control unit 30 that includes: a CPU that performs logical operations as a processor; a ROM in which an operation program necessary to control the apparatus is stored; a RAM in which data and the like are temporarily stored at the time of control; and the like, and controls the whole of the apparatus. The control unit 30 includes a computer installed with software. Functions of respective parts included in the control unit 30 are implemented by executing the software installed in the computer. The control unit 30 is connected to: a display part 45 that displays an X-ray image detected by the X-ray detector 42, or the like, such as a liquid crystal display panel; and an operation part 46 including a mouse, a keyboard, and the like for performing various types of operations.

Also, the control unit 30 includes: an image processing part 31 for image-processing an X-ray image detected by the X-ray detector 42 to display the processed image on the display part 45; a movement control part 32 for controlling the stage moving mechanism 44; an X-ray control part 33 for controlling the X-ray source 41; and an alarm display part 34 for performing the below-described alarm display.

Figure 2:
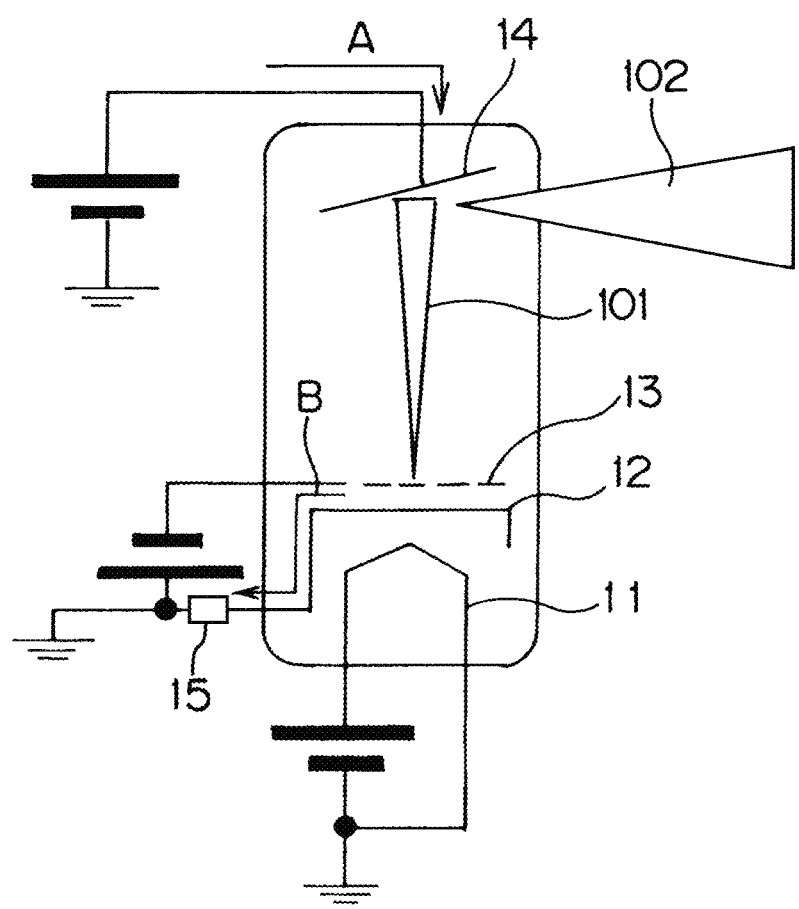
FIG. 2 is a schematic diagram of an X-ray source 41.

FIG. 2 is a schematic diagram of the X-ray source 41.

The X-ray source 41 is one provided with an indirectly-heated electron beam generating part, and includes: a cathode 12; a cathode heater 11 for heating the cathode 12; a grid electrode 13, and a target 14. An electron beam 101 generated from the cathode 12 heated by the cathode heater 11 is emitted from the cathode 12 toward the target 14 by the tube voltage between the cathode 12 and the target 14, collides with the target 14 after passing through the gird electrode 13, and thereby generates X-rays 102. At this time, target current A generated by electrons reaching the target 14 flows toward the target 14, and cathode current (emission current) B generated by electrons emitted from the cathode 12 flows from the cathode 12.

The cathode current B is detected by a cathode current detector 15 as tube current flowing through the X-ray source 41. Note that the target current A and the cathode current B usually match each other, and these currents correspond to the tube current. For this reason, instead of detecting the cathode current B as the tube current by the cathode current detector 15, a detector for the target current A may be disposed to measure a tube current value.

Figure 3:
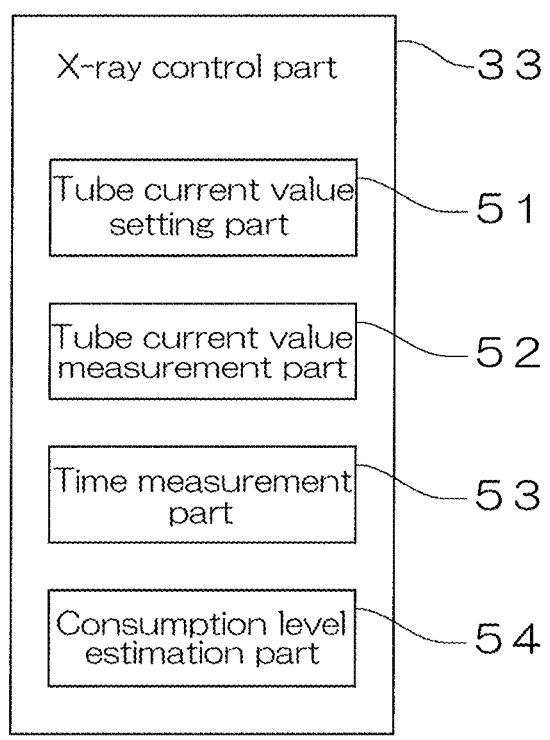
FIG. 3 is a functional block diagram of an X-ray control part 33 in a control unit 30.

FIG. 3 is a functional block diagram of the X-ray control part 33 in the control unit 30.

The X-ray control part 33 includes: a tube current value setting part 51 for setting the value of the tube current to be supplied to the X-ray source 41; a tube current value measurement part 52 that measures a cathode current value as the tube current value by the cathode current detector 15 illustrated in FIG. 2; a time measurement part 53 that measures the time when the tube current value is set by the tube current value setting part 51 and the time when the tube current value measured by the tube current value measurement part 52 reaches a set value; and a consumption level estimation part 54 that estimates the consumption level of the cathode 12 in the X-ray source 41 on the basis of the time until the tube current value reaches the set value after the tube current value has been set.

Figure 4:
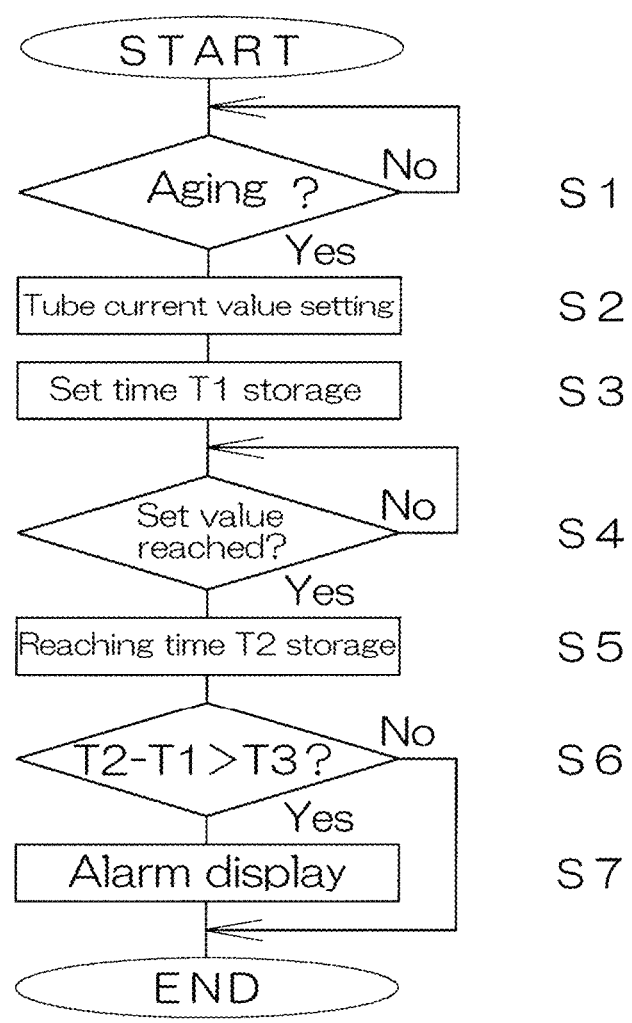
FIG. 4 is a flowchart illustrating one embodiment of a consumption level estimating operation for estimating the consumption level of a cathode 12 in the X-ray source 41.

A consumption level estimating operation for estimating the consumption level of the cathode 12 in the X-ray source 14 of the X-ray imaging apparatus having the above-described configuration will be described. FIG. 4 is a flowchart illustrating one embodiment of the consumption level estimating operation for estimating the consumption level of the cathode 12 in the X-ray source 41.

Note that in the following embodiment, at the time of aging (seasoning, warming up) of the X-ray source 41, the consumption level of the cathode 12 in the X-ray source 41 is estimated. The aging of the X-ray source 41 is one that, for example, must be performed at the start of a workday, and X-ray conditions at the time are constant, such as the tube voltage and the tube current. For this reason, the consumption level can be estimated under the same conditions, and the consumption level of the X-ray source 41 can be more accurately estimated. Note that the consumption level of the cathode 12 in the X-ray source 41 may be estimated at timing other than the aging time.

When estimating the consumption level of the cathode 12 in the X-ray source 41, it is determined whether or not to perform the aging (Step S1). Then, when performing the aging, the tube current value is set (Step S2). The setting of the tube current value is performed by the tube current value setting part 51 in the X-ray control part 33. In addition, the setting of the tube current value may be performed manually by an operator or performed by reading a preset value. Also, the time T1 when the tube current value is actually set is stored (Step S3).

In this state, the tube current value measurement part 52 in the X-ray control part 33 measures the tube current value using the cathode current detector 15. Then, it is waited until the actual tube current value reaches the set tube current value (Step S4). When the measured tube current value reaches the set value, the corresponding reaching time T2 is stored (Step S5).

After that, the time measurement part 53 in the X-ray control part 33 measures the time (T2-T1) until the actual tube current value reaches the set value after the tube current value has been set. Then, the consumption level estimation part 54 in the X-ray control part 33 estimates the consumption level of the cathode 12 in the X-ray source 41 on the basis of whether or not the time (T2-T1) is larger than a preset set time T3.

Figure 5:
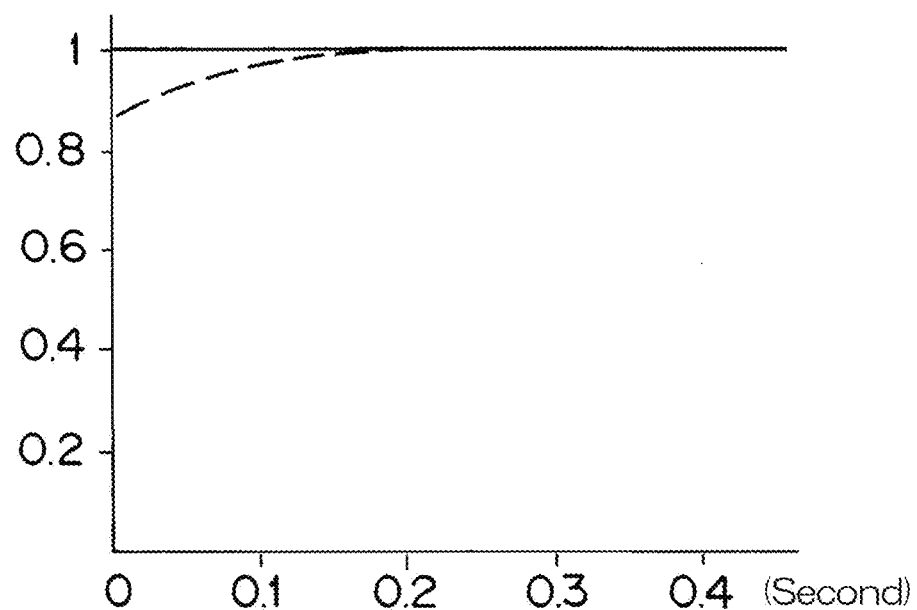
FIG. 5 is a graph illustrating the time until a tube current value reaches a set value.
Figure 6:
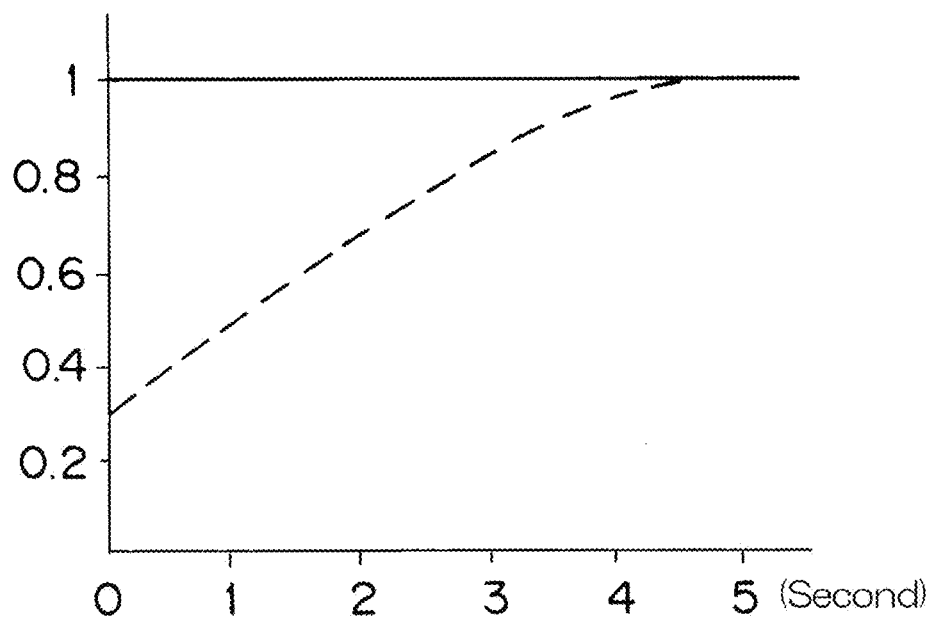
FIG. 6 is a graph illustrating the time until the tube current value reaches the set value.

FIGS. 5 and 6 are graphs illustrating the time until the tube current value reaches the set value. In addition, in these graphs, the horizontal axis represents time (second). Also, the vertical axis represents the tube current value with a target tube current value normalized to 1.

When the consumption level of the cathode 12 in the X-ray source 41 is low, as illustrated in FIG. 5, the time from the time when the tube current value was set, which corresponds to 0 on the horizontal axis in FIG. 5, to the time when the tube current value reached the set value is approximately 0.2 seconds. On the other hand, when the consumption level of the cathode 12 in the X-ray source 41 is high, as illustrated in FIG. 6, the time from the time when the tube current value was set, which corresponds to 0 on the horizontal axis in FIG. 6, to the time when the tube current value reached the set value is approximately 4.5 seconds.

When the cathode 12 in the X-ray source 41 is consumed, feedback control performed so that the tube current value matches the set value requires time until the tube current value reaches the set value. For this reason, by measuring the time from the time when the tube current value is set to the time when the tube current value reaches the set value, the consumption level of the cathode 12 can be estimated.

Referring to FIG. 4 again, when the time (T2-T1) until the actual tube current value reaches the set value after the tube current value has been set exceeds the preset set time T13 (Step S6), the consumption level estimation part 54 in the X-ray control part 33 transmits an alarm signal to the control unit 30. Then, upon receipt the alarm signal, the control unit 30 displays the alarm display on the display part 45 by action of the alarm display part illustrated in FIG. 1 (Step S7). Also, as necessary, alarm display using sound or the like is also performed. In doing so, the consumption of the cathode 12 can be preliminarily recognized.

In addition, in the above-described embodiment, as the X-ray source 41, the indirectly-heated type provided with the cathode heater 11 for heating the cathode 12 is used. However, the present invention may be applied to an X-ray source having a filament type cathode.

Also, the above-described embodiment employs a configuration in which, when the time until the tube current value reaches the set value exceed the preset set time T3, an alarm is displayed, but may employ a configuration in which the time when the tube current value is set and the time when the tube current value reaches the set value are displayed on the display part 45 or the like, and an operator checks them.

Further, the present invention may be adapted to preliminarily store the relationship between the time (T2-T1) until the actual tube current value reaches the set value after the tube current value has been set and the consumption level (e.g., %) of the cathode 12, and acquire and display a consumption level (%) corresponding to a measured time (T2-T1).

Further, in the above-described embodiment, the present invention is applied to the X-ray imaging apparatus. However, the X-ray source 41 itself may be disposed with the tube current value setting part that sets the tube current value and the time measurement part that measures the time when the tube current value is set and the time when the tube current value reaches the set value.

REFERENCE SIGNS LIST

11: Cathode heater
12: Cathode
13: Grid electrode
14: Target
15: Cathode current detector
30: Control unit
31: Image processing part
32: Movement control part
33: X-ray control part
34: Alarm display part
40: Casing
41: X-ray source
42: X-ray detector
43: Stage
44: Stage moving mechanism
45: Display part
46: Operation part
101: Electron beam
102: X-rays
A: Target current
B: Cathode current
W: Work

The invention claimed is:

1. An X-ray imaging apparatus comprising:
an X-ray source that gives high voltage between a cathode and a target, as well as keeps a tube current value at a set value by performing feedback control of a grid voltage given to a grid disposed between the cathode and the target;
a tube current value setting part that sets the set value on a tube current; and
a time measurement part that measures a first time interval between a first point in time when the set value is set under the feedback control and a second point in time when the tube current value reaches the set value for a first time after the first point in time under the feedback control; and
a consumption level estimation part that estimates a consumption level of the X-ray source based on the first time interval.

2. The X-ray imaging apparatus according to claim 1, comprising
an alarm display part that displays an alarm when the first time interval exceeds a preset second time interval.

3. The X-ray imaging apparatus according to claim 1, comprising
a control unit that, when performing aging on the X-ray source, performs measurement of the first time interval.

4. A consumption level estimation method for an X-ray source that gives high voltage between a cathode and a target, as well as keeps a tube current value at a set value by performing feedback control of a grid voltage given to a grid disposed between the cathode and the target,
the consumption level estimation method estimating a consumption level of the X-ray source based on a time interval between a first point in time when the set value is set under the feedback control and a second point in time when the tube current value reaches the set value for a first time after the first point in time under the feedback control.

* * * * *